United States Patent
Henderson et al.

(10) Patent No.: US 9,983,114 B2
(45) Date of Patent: May 29, 2018

(54) METHODS AND SYSTEMS FOR MONITORING LOADING OF AN AIR FILTER

(71) Applicant: Cummins, Inc., Columbus, IN (US)

(72) Inventors: Gregory H. Henderson, Columbus, IN (US); Andry Lesmana, Columbus, IN (US); W. Patrick Niehus, Columbus, IN (US); Alex Pama, Columbus, IN (US)

(73) Assignee: Cummins, Inc., Columbus, IN (US)

( * ) Notice: Subject to any disclaimer, the term of this patent is extended or adjusted under 35 U.S.C. 154(b) by 434 days.

(21) Appl. No.: 14/714,026

(22) Filed: May 15, 2015

(65) Prior Publication Data

US 2015/0330857 A1 Nov. 19, 2015

Related U.S. Application Data

(60) Provisional application No. 61/993,450, filed on May 15, 2014.

(51) Int. Cl.

| | |
|---|---|
| *G01B 5/28* | (2006.01) |
| *G01N 15/08* | (2006.01) |
| *G01L 13/00* | (2006.01) |
| *B01D 46/00* | (2006.01) |
| *F02M 35/09* | (2006.01) |
| *G06F 11/30* | (2006.01) |
| *B01D 46/44* | (2006.01) |

(52) U.S. Cl.
CPC ..... *G01N 15/0826* (2013.01); *B01D 46/0086* (2013.01); *F02M 35/09* (2013.01); *G01L 13/00* (2013.01); *B01D 46/444* (2013.01); *B01D 46/446* (2013.01); *G01N 2015/084* (2013.01)

(58) Field of Classification Search
CPC .................................................. G01N 15/0826
See application file for complete search history.

(56) References Cited

U.S. PATENT DOCUMENTS

| | | |
|---|---|---|
| 4,751,501 A | 6/1988 | Gut |
| 5,036,698 A | 8/1991 | Conti |
| 6,505,505 B1 * | 1/2003 | Henzinger ............. G01F 1/684 73/114.18 |
| 7,591,173 B2 | 9/2009 | Benscoter et al. |
| 8,327,695 B2 | 12/2012 | Jackson et al. |
| 2003/0221480 A1 * | 12/2003 | Aschner ................ F02M 35/09 73/114.34 |
| 2011/0197580 A1 | 8/2011 | Andrasko et al. |
| 2011/0308308 A1 | 12/2011 | Herman et al. |

(Continued)

*Primary Examiner* — Phuong Huynh
(74) *Attorney, Agent, or Firm* — Foley & Lardner LLP

(57) ABSTRACT

Methods and systems for estimating the loading of an air filter are disclosed herein. The method includes receiving upstream mass air flow data indicative of a mass air flow on an upstream side of an air filter (i.e., the "dirty side of the filter"), receiving downstream air pressure data indicative of an air pressure on a downstream side of the air filter (i.e., the "clean side of the filter"), and receiving downstream temperature data indicative of a temperature on the downstream side of the air filter. The method also includes determining a differential pressure (ΔP) across the air filter indicative of a loading of the air filter based on the upstream mass air flow data, the downstream air pressure data, and the downstream temperature data.

17 Claims, 12 Drawing Sheets

(56) References Cited

U.S. PATENT DOCUMENTS

2012/0197550 A1\* 8/2012 Cianflone ........... F02D 41/0065
702/45
2012/0317974 A1 12/2012 Rollinger \* cited by examiner

METHODS AND SYSTEMS FOR MONITORING LOADING OF AN AIR FILTER

CROSS REFERENCE TO RELATED APPLICATIONS

This application claims the benefit of U.S. Provisional Patent Application No. 61/993,450 entitled, "METHODS AND SYSTEMS FOR MONITORING LOADING OF AN AIR FILTER," May 15, 2014, which is incorporated herein by reference in its entirety.

TECHNICAL FIELD

This disclosure relates to air filters. In particular, this disclosure relates to methods and systems for monitoring the loading of an air filter for an engine by determining a rated flow differential pressure across the air filter.

BACKGROUND

Engines generally utilize air filters for removing debris from air supplied to the engines. An engine may experience engine failure if the air filter becomes clogged and insufficient air flow is able to pass through the clogged filter. One method for monitoring clogging, otherwise referred to as "loading," is by measuring the differential air pressure across the filter. This may be done by providing an air pressure sensor on the upstream side of the filter (i.e., the "dirty side of the filter") and an air pressure sensor on the downstream side of the filter (i.e., the "clean side of the filter"). The difference in air pressure across the filter as determined by these sensors, or $\Delta P$, may be used to assess loading of the air filter. However, this "two sensor" approach adds cost and complexity to an air filter system. A less expensive and less complex system for monitoring loading of an air filter is desirable.

SUMMARY

Disclosed herein are methods and systems for monitoring loading of an air filter by estimating a rated flow differential pressure across the air filter and providing an indication of the monitored loading when the air filter should be replaced.

One embodiment relates to a method for estimating a loading of an air filter. The method includes receiving upstream mass air flow data indicative of a mass air flow on an upstream side of an air filter (i.e., the "dirty side of the filter"), receiving downstream air pressure data indicative of an air pressure on a downstream side of the air filter (i.e., the "clean side of the filter"), and receiving downstream temperature data indicative of a temperature on the downstream side of the air filter. The method also includes determining a differential pressure ($\Delta P$) across the air filter indicative of a loading of the air filter based on the upstream mass air flow data, the downstream air pressure data, and the downstream temperature data.

Another embodiment relates to a system for estimating a loading of an air filter. The system includes a mass air flow sensor configured to measure a plurality of mass air flows on an upstream side of an air filter, an air pressure sensor disposed on a downstream side of the air filter and configured to measure a plurality of air pressures on the downstream side, and a temperature sensor disposed on the downstream side of the air filter and configured to measure a plurality of temperatures on the downstream side. The system also includes a processing system communicably coupled to the mass air flow sensor, the air pressure sensor, and the temperature sensor, and configured to determine a differential pressure ($\Delta P$) across the air filter indicative of a loading of the air filter based on the plurality of mass air flows, the plurality of air pressures, and the plurality of temperatures Still another embodiment relates to an apparatus for estimating a loading of an air filter. The apparatus includes an upstream mass air flow module structured to receive upstream mass air flow data indicative of a mass air flow on an upstream side of an air filter, a downstream air pressure module structured to receive downstream air pressure data indicative of an air pressure on a downstream side of the air filter, and a downstream temperature module structured to receive downstream temperature data indicative of a temperature on the downstream side of the air filter. The apparatus also includes a differential pressure module structured to determine a differential pressure ($\Delta P$) across the air filter indicative of a loading of the air filter based on the upstream mass air flow data, the downstream air pressure data, and the downstream temperature data.

These and other features, together with the organization and manner of operation thereof, will become apparent from the following detailed description when taken in conjunction with the accompanying drawings.

DETAILED DESCRIPTION

Figure 1:
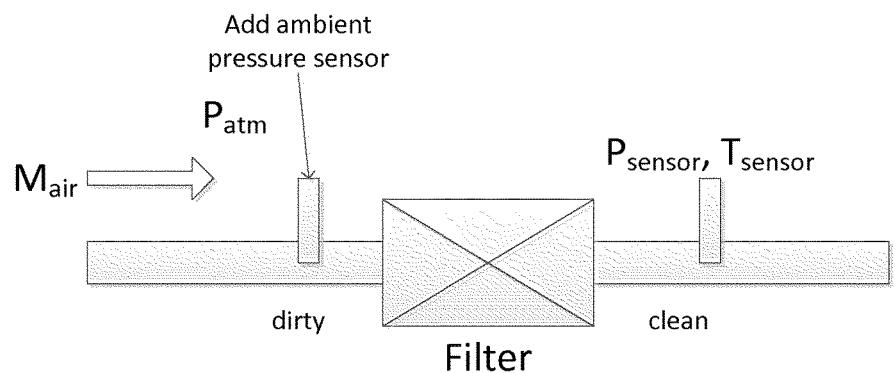
FIG. 1 is a schematic view of a two-sensor approach for monitoring the loading of an air filter.

Referring to the figures generally, the various embodiments disclosed herein relate to methods and systems for estimating the loading of an air filter. Loading, otherwise referred to as clogging, may be estimated from the differential air pressure across the filter. In a two-sensor approach, the differential air pressure is obtained by measuring the air pressures on the upstream side of the filter (i.e., the "dirty side of the filter") and the downstream side of the filter (i.e., the "clean side of the filter") with two air pressure sensors, as shown in FIG. 1. However, this two-sensor approach adds cost and complexity to the air filter system. The methods and systems disclosed herein provide a less expensive and less complex approach for estimating the loading of the air filter. Methods and systems disclosed herein were developed to estimate the air filter differential pressure using a given engine air flow, filter clean-side pressure, and filter clean-side temperature. The process is capable of adapting to both laminar and turbulent pressure losses and is thus insensitive to the type of debris loading the filter and housing design. The method may be relatively easy to calibrate, and only the filter constant, Cramer's rule denominator, and minimum air flow thresholds may be determined empirically.

Figure 2:
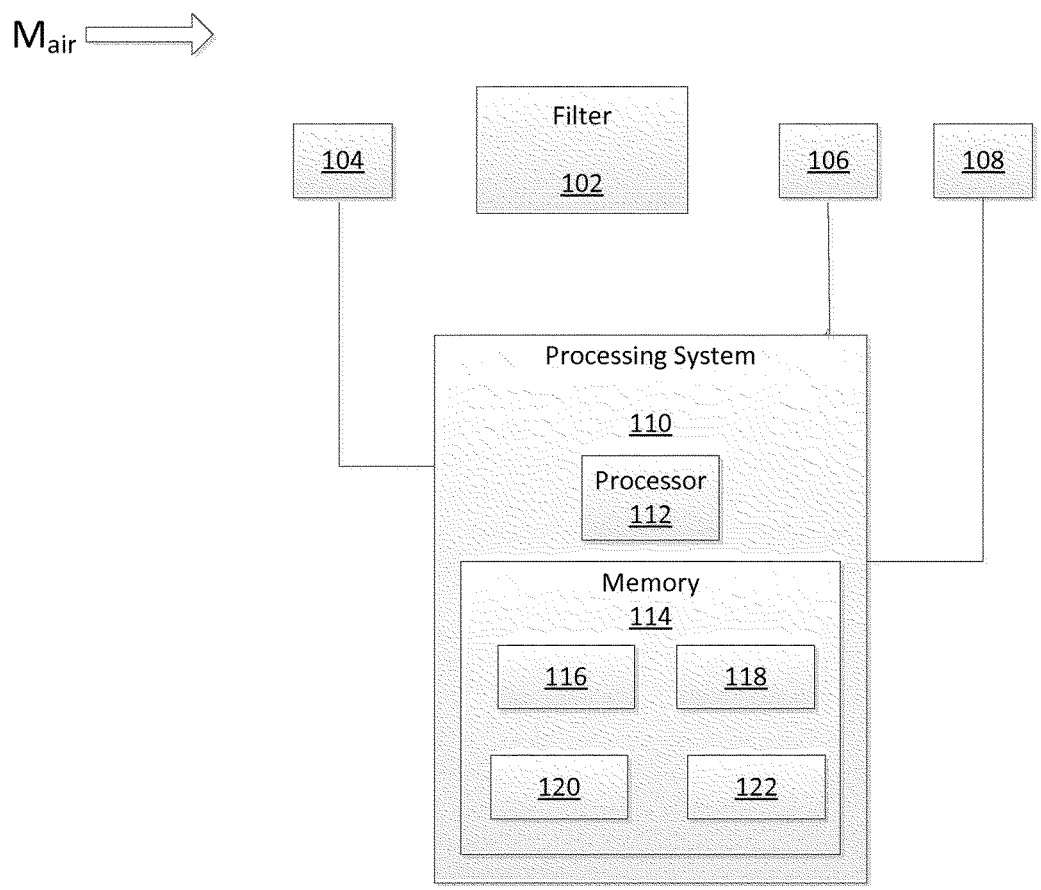
FIG. 2 is a schematic view of a system for estimating the loading of an air filter according to an example embodiment.

Referring to FIG. 2, a system 100 for estimating the loading of an air filter 102 is shown according to an exemplary embodiment. The system 100 includes a mass air flow sensor 104 on the upstream side of the air filter 102 (i.e., the "dirty side"), a pressure sensor 106 on the downstream side of the air filter 102 (i.e., the "clean side"), a temperature sensor 108 on the downstream side, and a processing system 110. It shall be appreciated that although a physical mass air flow sensor 104 is utilized to measure the mass air flow in the example, the air flow may be monitored via a virtual sensor. The virtual sensor may uses various data pieces indicative of the air flow in the engine. For example, the virtual sensor may use one or more lookup tables, models, algorithms, processes, etc.

As shown, the processing system 110 is communicably coupled to the mass air flow sensor 104, the pressure sensor 106, and the temperature sensor 108. Communication between and among the components may be via any number of wired or wireless connections. For example, a wired connection may include a serial cable, a fiber optic cable, a CAT5 cable, or any other form of wired connection. In comparison, a wireless connection may include the Internet, Wi-Fi, cellular, radio, etc. In one embodiment, a controller area network (CAN) bus provides the exchange of signals, information, and/or data. The CAN bus includes any number of wired and wireless connections. Because the processing system 110 is communicably coupled to the systems and components in the system 100 of FIG. 2, the processing system 110 is structured to receive data (e.g., signals, values, etc.) from one or more of the components shown in FIG. 2.

The processing system 110 is shown to include a processor 112 and a memory 114. The processor 112 may be implemented as a general-purpose processor, an application specific integrated circuit (ASIC), one or more field programmable gate arrays (FPGAs), a digital signal processor (DSP), a group of processing components, or other suitable electronic processing components. The one or more memory devices 114 (e.g., RAM, ROM, Flash Memory, hard disk storage, etc.) may store data and/or computer code for facilitating the various processes described herein. Thus, the one or more memory devices 114 may be communicably connected to the processor 112 and provide computer code or instructions to the processor 112 for executing the processes described in regard to the processor 112 herein. Moreover, the one or more memory devices 114 may be or include tangible, non-transient volatile memory or non-volatile memory. Accordingly, the one or more memory devices 114 may include database components, object code components, script components, or any other type of information structure for supporting the various activities and information structures described herein.

The memory 114 is shown to include an upstream mass air flow module 116 structured to receive the upstream mass air flow data, a downstream air pressure module 118 structured to receive the downstream air pressure data, a downstream temperature module 120 structured to receive the downstream temperature data, and a differential pressure module 122 structured to determine the differential pressure across the air filter. In some embodiments, the memory 114 further includes an indication module (not shown in the present figure) structured to compare the determined differential pressure with a reference value and to determine a status of the air filter based on the comparison. While various modules with particular functionality are shown in FIG. 2, it should be understood that the processing system 110 may include any number of modules for completing the functions described herein. For example, the activities of multiple modules may be combined as a single module, as additional modules with additional functionality may be included, etc. Further, it should be understood that the processing system 110 may further control other vehicle activity beyond the scope of the present disclosure.

Certain operations of the processing system 110 described herein include operations to interpret and/or to determine one or more parameters. Interpreting or determining, as utilized herein, includes receiving values by any method known in the art, including at least receiving values from a datalink or network communication, receiving an electronic signal (e.g. a voltage, frequency, current, or PWM signal) indicative of the value, receiving a computer generated parameter indicative of the value, reading the value from a memory location on a non-transient computer readable storage medium, receiving the value as a run-time parameter by any means known in the art, and/or by receiving a value by which the interpreted parameter can be calculated, and/or by referencing a default value that is interpreted to be the parameter value.

Figure 3:
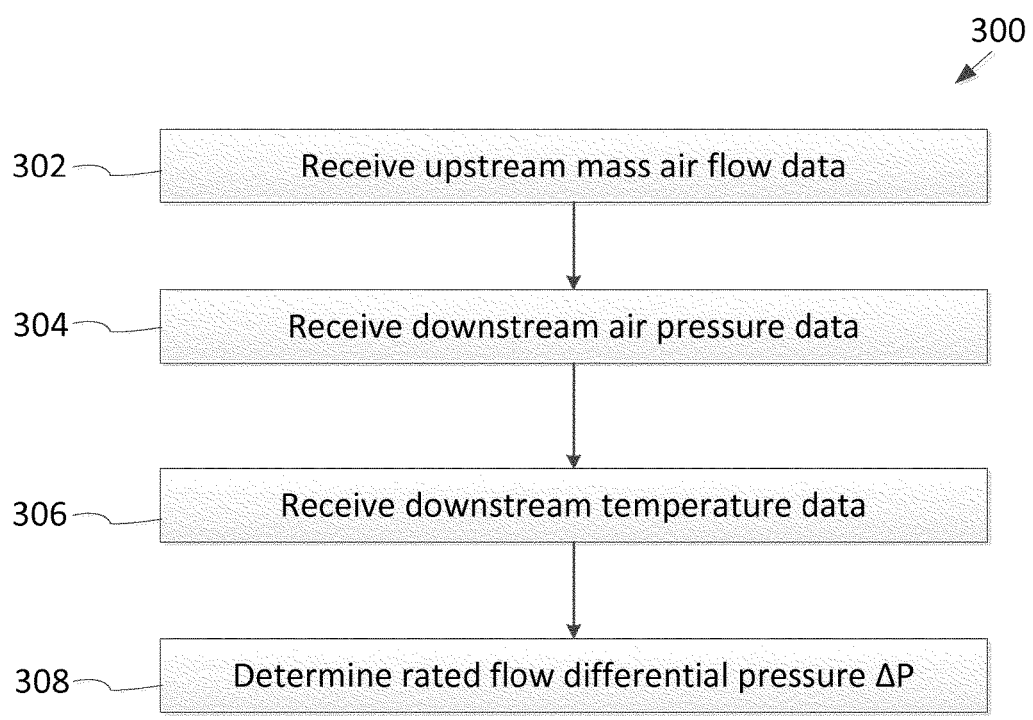
FIG. 3 is a flow chart of a method for estimating the loading of an air filter according to an example embodiment.

Referring to FIG. 3, a flow chart of a method for estimating the loading of an air filter is shown according to an exemplary embodiment. At operation 302, data indicative of a mass air flow on the upstream side of the air filter (i.e., upstream mass air flow data) are received from, for example, a mass air flow sensor disposed on the upstream side. The operation 302 may be performed by the upstream mass air flow module 116 of FIG. 2. In certain embodiments, the upstream mass air flow data is determined, estimated, modeled, etc. from operation data regarding operation of the engine. For example and in regard to this virtual sensor embodiment, the processing system may utilize an engine speed and an engine throttle position to estimate the upstream mass air flow. In other embodiments, a combination of a virtual sensor and a physical sensor may be utilized by the controller to determine or estimate an upstream mass air flow. At operation 304, data indicative of an air pressure on the downstream side of the air filter (i.e., downstream air pressure data) are received from, for example, an air pressure sensor disposed on the downstream side. The operation 304 may be performed by the downstream air pressure module 118 of FIG. 2. At operation 306, data indicative of a temperature on the downstream side of the air filter (i.e., downstream temperature data) are obtained from, for example, a temperature sensor disposed on the downstream side. The operation 306 may be performed by the downstream temperature module 120 of FIG. 2. At operation 308, the rated flow differential pressure ΔP is calculated based on the received upstream mass air flow data, downstream air pressure data, and downstream temperature data. The operation 308 may be performed by the differential pressure module 122 of FIG. 2. In some embodiments, the method may further include an operation performed by the indication module in which the determined differential pressure is compared with a reference value and a status of the air filter is determined based on the comparison.

In some embodiments, the rated flow differential pressure ΔP is calculated as:

$$\Delta P = P_{amb} - P_{sensor} = \frac{1}{\rho}(C_1 M + C_2 M^2), \quad (1)$$

The rated flow differential pressure, ΔP, represents the air pressure difference between the upstream side and the downstream side of the air filter when the air flow on the upstream side is at a designed operating flow M (also called a "rated flow"). In equation (1), $P_{amb}$ is an air pressure of the upstream side of the air filter, $P_{sensor}$ is the air pressure of the downstream side of the air filter obtained from the air pressure sensor. The pressure drop through the air filter has both a laminar and a turbulent pressure drop mechanism due to the filter element, the bend, and pipe losses. In equation (1), $C_1$ is a coefficient representing a laminar pressure loss, and $C_2$ is a coefficient representing a turbulent pressure loss. ρ is an air density of the downstream side of the air filter calculated as:

$$\rho = \frac{P_{sensor}}{RT}, \quad (2)$$

wherein T is the temperature of the downstream side of the air filter obtained from a temperature sensor, and R is a gas constant.

In some embodiments, the coefficients $C_1$ and $C_2$ are determined by applying a least squares method to a plurality of mass air flows on the upstream side, a plurality of air pressure on the downstream side, and a plurality of temperatures on the downstream side. An error function may be constructed as follows:

$$E^2 = \Sigma_i (k_i P_{sensor,i}^2 - k_i P_{sensor,i} P_{amb} - C_1 M_i - C_2 M_i^2)^2, \quad (3)$$

wherein $M_i$ is an i-th mass air flow of the plurality of mass air flows obtained from the mass air flow sensor, $P_{sensor,i}$ is an i-th air pressure of the plurality of air pressures obtained from the air pressure sensor. $k_i$ is calculated as $$k_i = 1000/(RT_i), \quad (4)$$

wherein $T_i$ is an i-th temperature of the plurality of temperatures obtained from the temperature sensor.

Taking the partial derivative of the error function with respect to each of the unknown coefficients $P_{amb}$, $C_1$, and $C_2$ and setting each equal to zero yields the following matrix equation:

$$\begin{bmatrix} \sum k_i^2 P_{sensor,i}^3 \\ -\sum k_i P_{sensor,i}^2 M_i \\ -\sum k_i P_{sensor,i}^2 M_i^2 \end{bmatrix} = \quad (5)$$

$$\begin{bmatrix} \sum k_i^2 P_{sensor,i}^2 & -\sum k_i P_{sensor,i} M_i & -\sum k_i P_{sensor,i} M_i^2 \\ -\sum k_i P_{sensor,i} M_i & \sum M_i^2 & \sum M_i^3 \\ -\sum k_i P_{sensor,i} M_i^2 & \sum M_i^3 & \sum M_i^4 \end{bmatrix} \begin{bmatrix} P_{amb} \\ C_1 \\ C_2 \end{bmatrix},$$

Using average [ ] to replace Σ yields:

$$\begin{bmatrix} [k_i^2 P_{sensor,i}^3] \\ [-k_i P_{sensor,i}^2 M_i] \\ [-k_i P_{sensor,i}^2 M_i^2] \end{bmatrix} = \quad (6)$$

$$\begin{bmatrix} [k_i^2 P_{sensor,i}^2] & [-k_i P_{sensor,i} M_i] & [-k_i P_{sensor,i} M_i^2] \\ [-k_i P_{sensor,i} M_i] & [M_i^2] & [M_i^3] \\ [-k_i P_{sensor,i} M_i^2] & [M_i^3] & [M_i^4] \end{bmatrix} \begin{bmatrix} P_{amb} \\ C_1 \\ C_2 \end{bmatrix},$$

$P_{amb}$, $C_1$ and $C_2$ may be determined as follows by applying Cramer's Rule to equation (6):

$$P_{amb} = \frac{\text{Det}\begin{bmatrix} [k_i^2 P_{sensor,i}^3] & [-k_i P_{sensor,i} M_i] & [-k_i P_{sensor,i} M_i^2] \\ [-k_i P_{sensor,i}^2 M_i] & [M_i^2] & [M_i^3] \\ [-k_i P_{sensor,i}^2 M_i^2] & [M_i^3] & [M_i^4] \end{bmatrix}}{\text{Den}}, \quad (7)$$

$$C_1 = \frac{\text{Det}\begin{bmatrix} [k_i^2 P_{sensor,i}^2] & [k_i^2 P_{sensor,i}^3] & [-k_i P_{sensor,i} M_i^2] \\ [-k_i P_{sensor,i} M_i] & [-k_i P_{sensor,i}^2 M_i] & [M_i^3] \\ [-k_i P_{sensor,i} M_i^2] & [-k_i P_{sensor,i}^2 M_i^2] & [M_i^4] \end{bmatrix}}{\text{Den}},$$

$$C_2 = \frac{\text{Det}\begin{bmatrix} [k_i^2 P_{sensor,i}^2] & [-k_i P_{sensor,i} M_i] & [k_i^2 P_{sensor,i}^3] \\ [-k_i P_{sensor,i} M_i] & [M_i^2] & [-k_i P_{sensor,i}^2 M_i] \\ [-k_i P_{sensor,i} M_i^2] & [M_i^3] & [-k_i P_{sensor,i}^2 M_i^2] \end{bmatrix}}{\text{Den}},$$

$$\text{Den} = \text{Det}\begin{bmatrix} [k_i^2 P_{sensor,i}^2] & [-k_i P_{sensor,i} M_i] & [-k_i P_{sensor,i} M_i^2] \\ [-k_i P_{sensor,i} M_i] & [M_i^2] & [M_i^3] \\ [-k_i P_{sensor,i} M_i^2] & [M_i^3] & [M_i^4] \end{bmatrix},$$

wherein Den is a denominator and Det[matrix] is the determinant of the matrix:

$$\text{Det}\begin{bmatrix} a_{11} & a_{12} & a_{13} \\ a_{21} & a_{21} & a_{21} \\ a_{31} & a_{31} & a_{31} \end{bmatrix} =$$

$$a_{11}a_{22}a_{33} + a_{21}a_{32}a_{13} + a_{31}a_{23}a_{12} - (a_{13}a_{22}a_{31} + a_{23}a_{32}a_{11} + a_{33}a_{21}a_{12})$$

It shall be appreciated that the above equations are for illustration, not meant to be limitations. Other formulas, processes, models, etc. may be used in conjunction or independent of the equations listed herein above.

Figure 4:
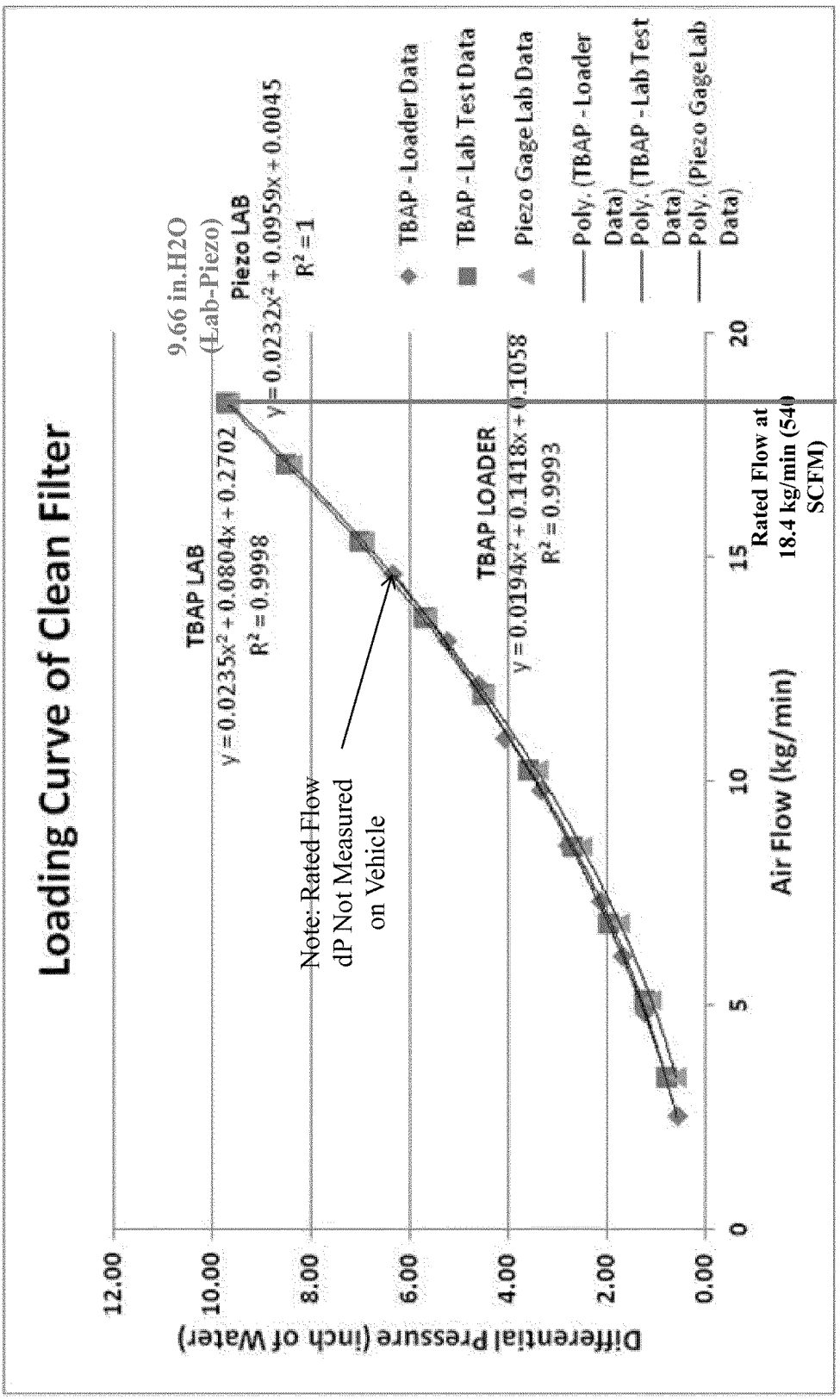
FIG. 4 is a graph illustrating the results of a loading curve for a clean filter, according to an example embodiment.
Figure 5:
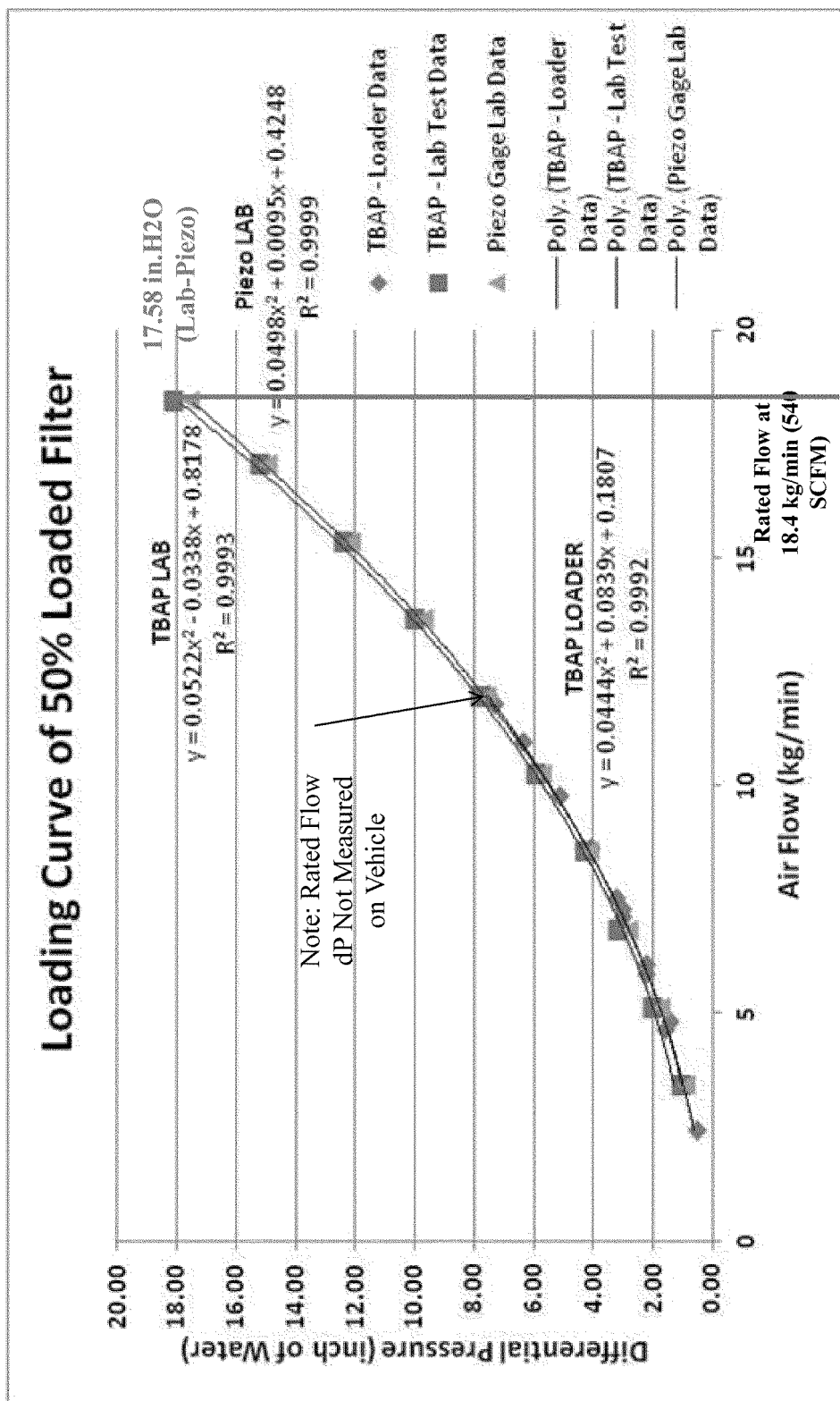
FIG. 5 is a graph illustrating the results of a loading curve of a 50% loaded filter, according to an example embodiment.
Figure 6:
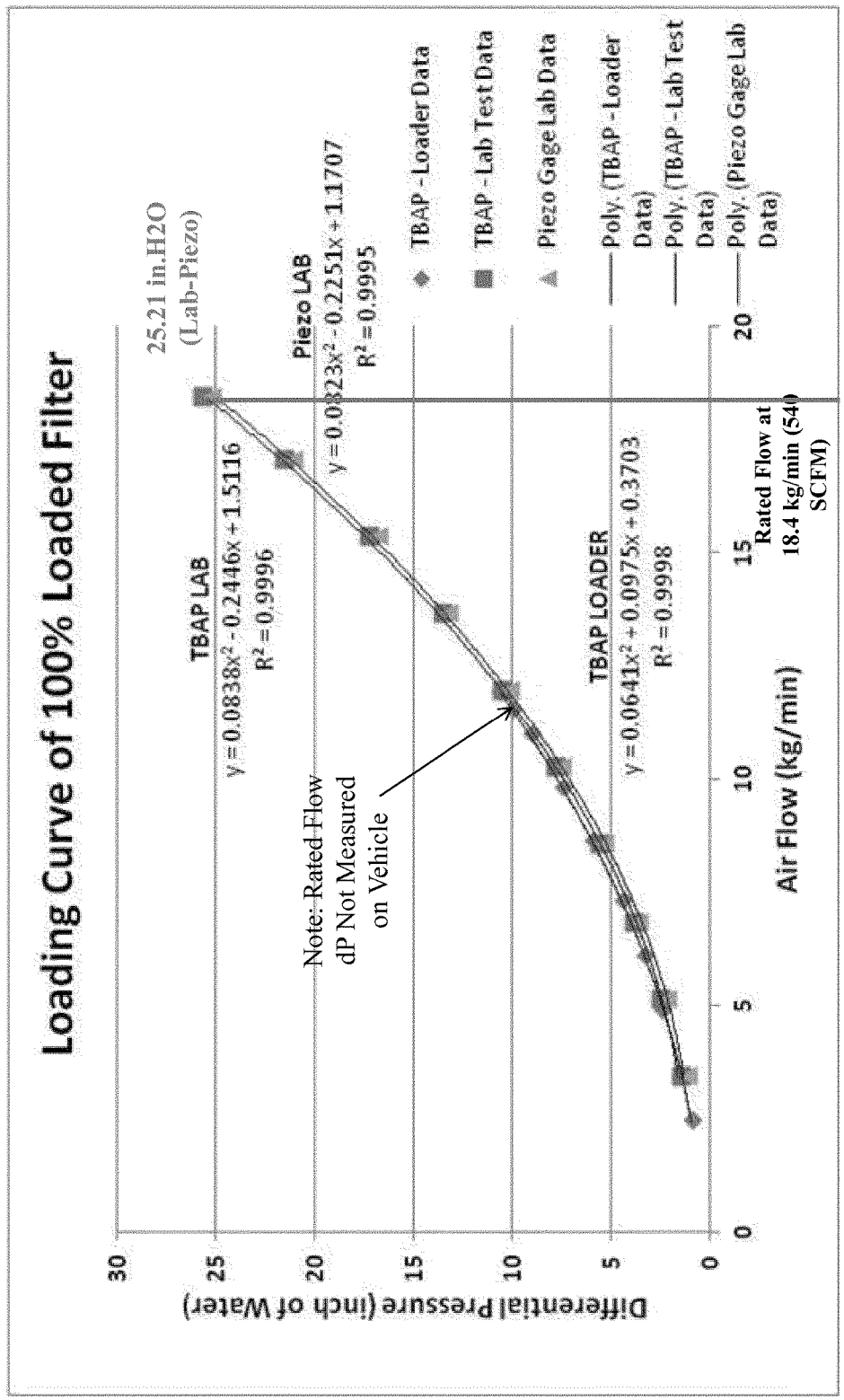
FIG. 6 is a graph illustrating the results of a loading curve of a 100% loaded filter, according to an example embodiment.

FIGS. 4-6 are graphs illustrating the results of the least squares fit of loading curves for filters with different loadings. Three air filter boxes having known debris loading were obtained: a clean filter, a 50% loaded filter; and a 100% loaded filter. These air filter boxes were flow tested on a bench rig, so that the expected pressure drop at the rated flow could be quantified. Each filter was installed on a loader vehicle and various cycles (i.e., "static" or "dynamic") were run while recording the algorithm input data. The input data was post-processed through the mathematical equations programmed into a post-processing medium, such as Microsoft Excel®. FIG. 4 illustrates the results of the least squares fit of loading curves for a clean filter. FIG. 5 illustrates the results for a 50% loaded filter. FIG. 6 illustrates the results for a 100% loaded filter.

Figure 7:
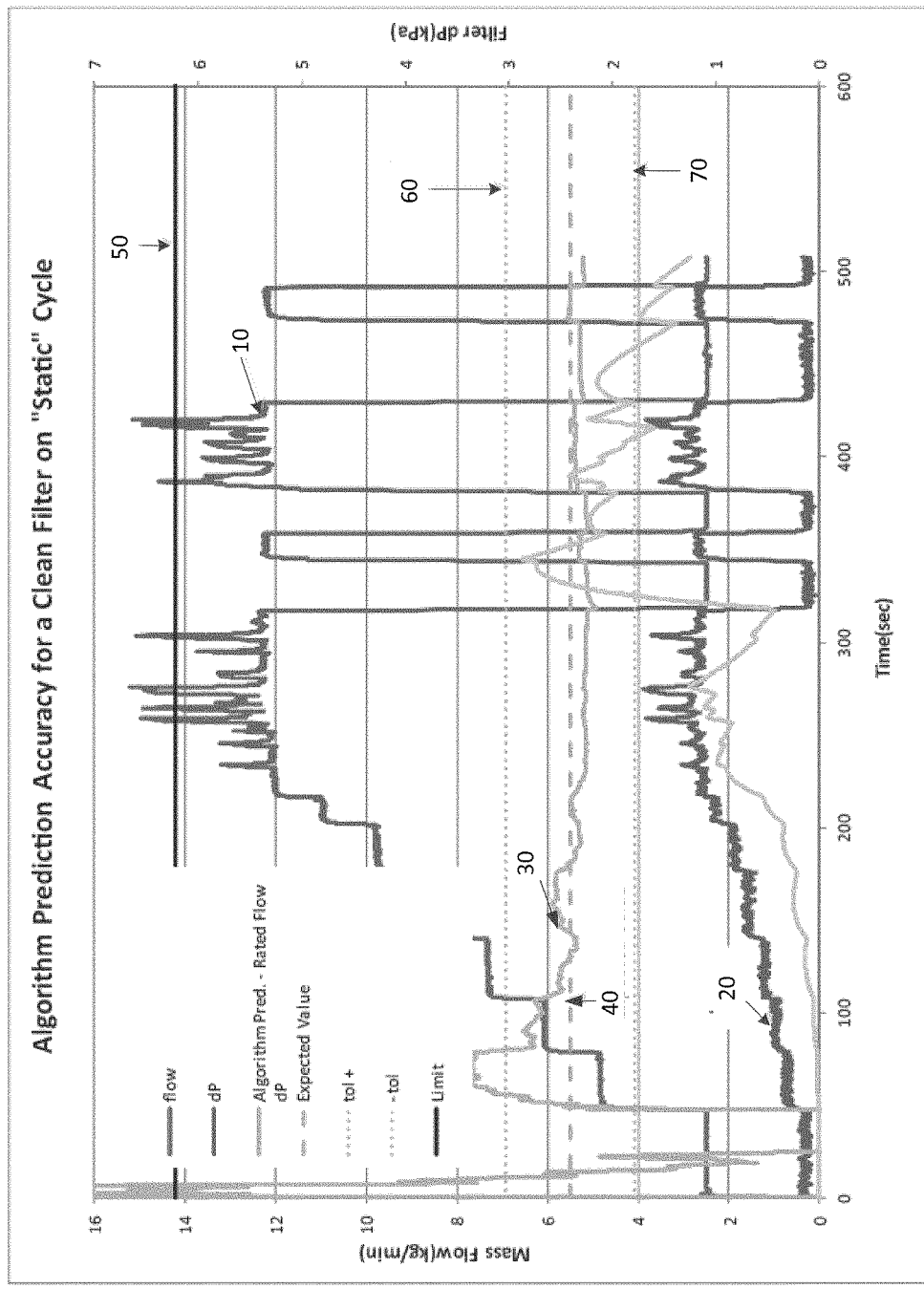
FIG. 7 is a graph illustrating the accuracy of the method of FIG. 3 for estimating $\Delta P$ for a clean filter on a "static" cycle according to an example embodiment.
Figure 8:
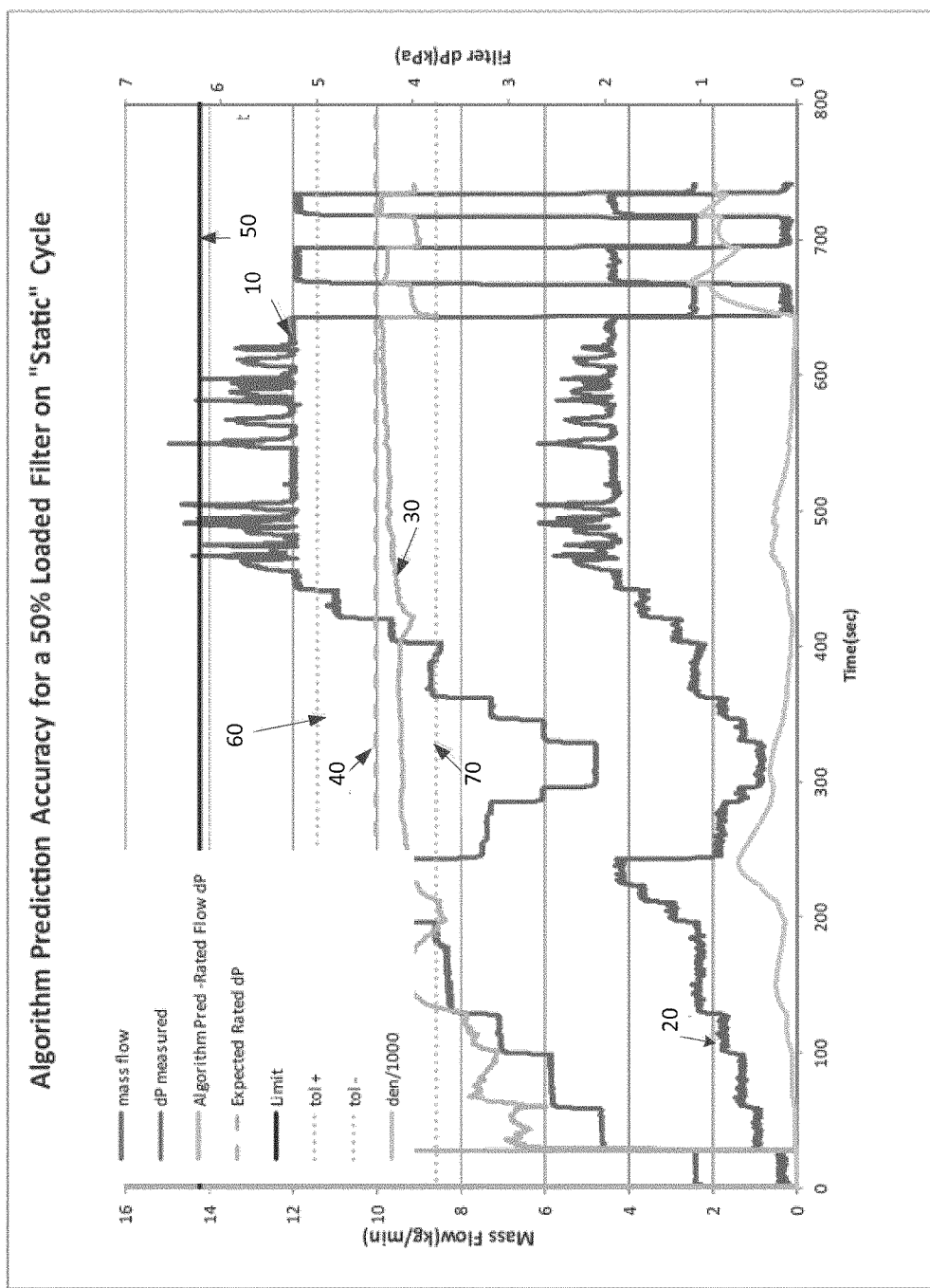
FIG. 8 is a graph illustrating the accuracy of the method of FIG. 3 for estimating $\Delta P$ for a given air mass flow for a 50% loaded filter on a "static" cycle according to an exemplary embodiment.
Figure 9:
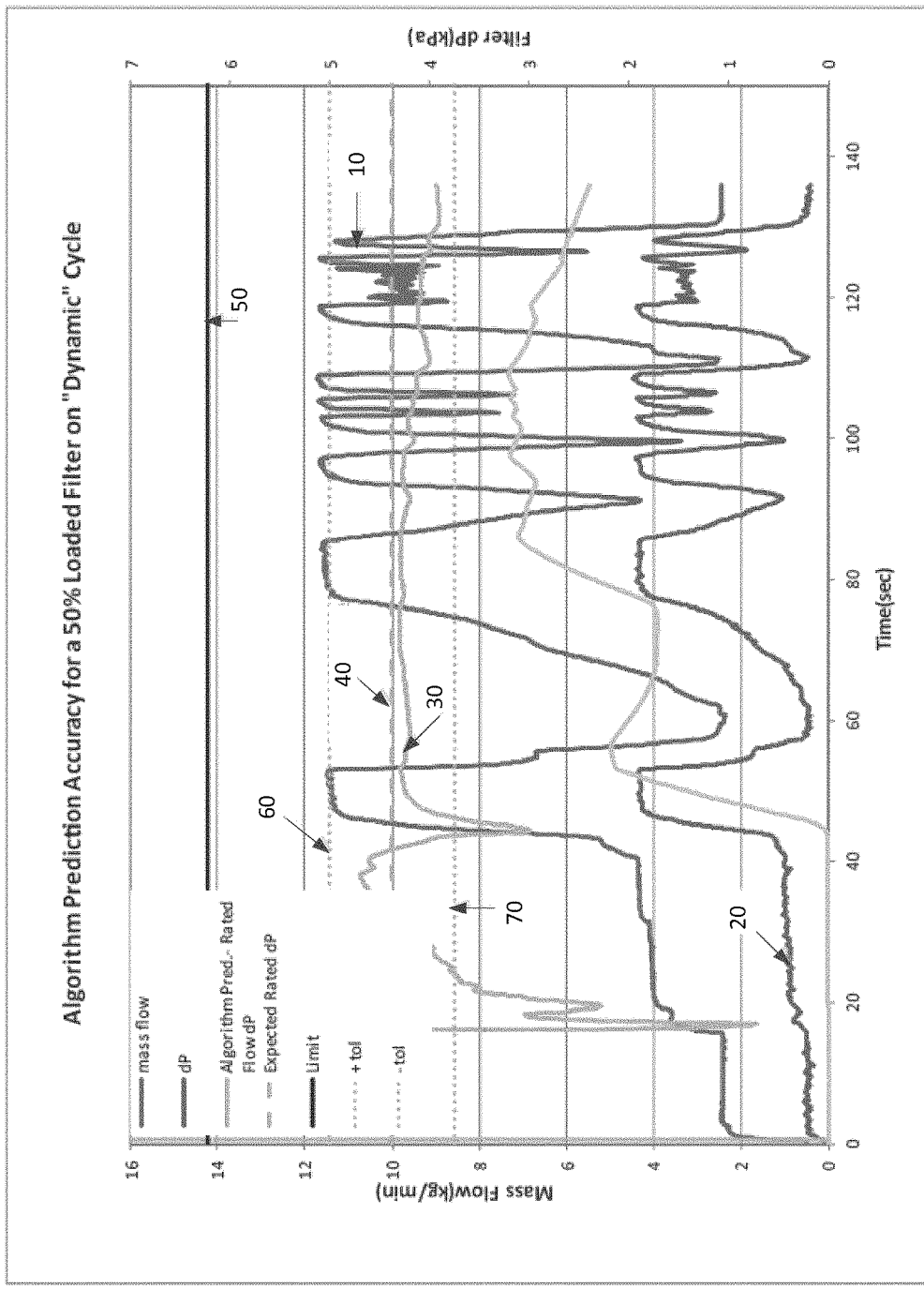
FIG. 9 is a graph illustrating the accuracy of the method of FIG. 3 for estimating $\Delta P$ for a given air mass flow for a 50% loaded filter on a "dynamic" cycle according to an exemplary embodiment.
Figure 10:
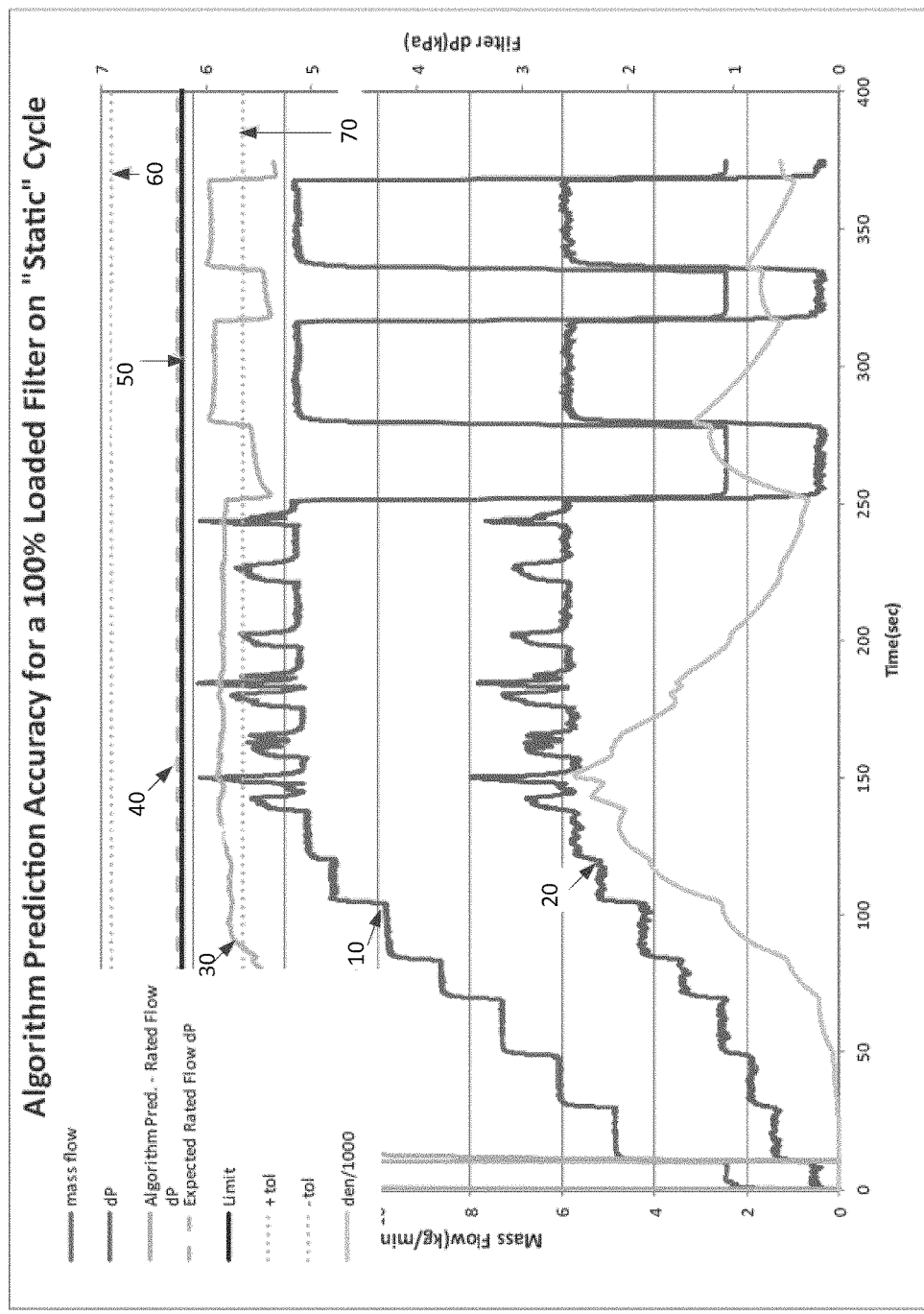
FIG. 10 is a graph illustrating the accuracy of the method of FIG. 3 for estimating $\Delta P$ for a given air mass flow for a 100% loaded filter on a "static" cycle according to an exemplary embodiment.
Figure 11:
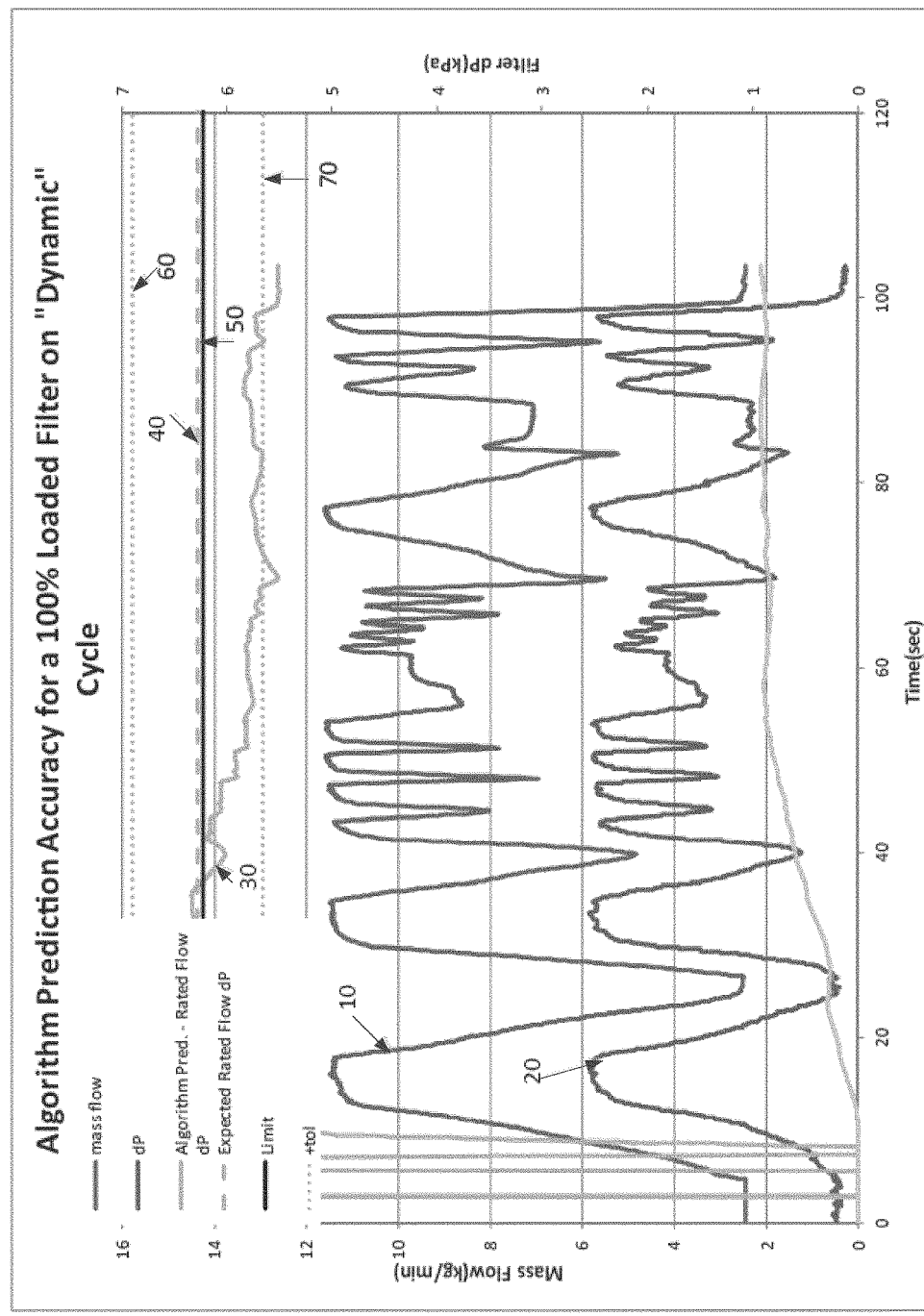
FIG. 11 is a graph illustrating the accuracy of the method of FIG. 3 for estimating $\Delta P$ for a given air mass flow for a 100% loaded filter on a "dynamic" cycle according to an exemplary embodiment.

FIGS. 7-11 are graphs illustrating the accuracy of the method of FIG. 3 for estimating rated flow differential pressure ΔP at different filter situations. Specifically, FIG. 7 illustrates the accuracy of the method for estimating ΔP for a clean filter on a "static" cycle. FIG. 8 illustrates the accuracy for a 50% loaded filter on a "static" cycle. FIG. 9 illustrates the accuracy for a 50% loaded filter on a "dynamic" cycle. FIG. 10 illustrates the accuracy for a 100% loaded filter on a "static" cycle. FIG. 11 illustrates the accuracy for a given air mass flow for a 100% loaded filter on a "dynamic" cycle. As used herein, a static cycle means a steady state and a dynamic cycle means a transient state. For example, a constant engine speed for a calibratable amount of time may indicate a steady state. Or, an engine torque below a predetermined threshold may indicate a steady state. Conversely, torques above the threshold and speeds may be sinusoidal in nature may indicate a dynamic or changing cycle. In FIGS. 7-11, curve 10 represents the mass air flow on the upstream side of the air filter. Curve 20 represents the differential pressure across the air filter that changes with the upstream mass air flow. Curve 30 represents the rated flow differential pressure determined by the method of FIG. 3. Curve 40 represents the expected value of rated flow differential pressure. Line 50 represents the clogging limit of the air filter. Line 60 represents the +10% error of the expected value of rated flow differential pressure. Line 70 represents the −10% error of the expected value of rated flow differential pressure.

In some embodiments, the estimated ΔP may be compared with a reference value (e.g., a reference ΔP for a rated air mass flow) and a status of the air filter may be determined based on the comparison. For example, the status is healthy responsive to the differential pressure being less than the reference value. This determination indicates that air is substantially freely moving from the filter (e.g., little or inconsequential clogging occurring). A healthy status may also be indicated by a determined pressure different being at a or below a certain threshold, being within a certain range, and the like. In certain embodiments, the threshold or range for a healthy status indication may change as a function of one or more engine, vehicle, and/or air filter operating parameters. For example, at low engine speeds, a relatively higher amount of clogging is permitted than at higher engine speeds (e.g., greater than 1000 RPM). Accordingly, a variety of guidelines, parameters, definitions, and the like may be used to determine that the air filter is healthy based on the determined pressure differential. The status may also include at least one of replace and check. In one embodiment, the status of at least one replace and check is in response to the differential pressure being greater than or equal to the reference value. When the differential pressure is greater than or equal to a reference value, than clogging beyond a predefined allowable amount is determined to be occurring (the predetermined allowable amount is based on the prescribed reference value). While a reference value or threshold may be used in some embodiments, in other configurations, a range may be used. Similar to a healthy status determination, the range corresponding to replacement and check statuses may change as a function of at least one of the engine, vehicle, and/or air filter operating parameters. In some embodiments, the status is replace if the differential pressure is greater than the reference value by a first amount and the status is check if the differential pressure is greater than the reference value by a second amount, where the first amount being greater than the second amount. In this example, replacement corresponds with the relatively more severe potential condition, such that if the differential pressure is above the higher threshold (or within the higher range, etc.), an operator may be alerted that the filter should be replaced and at a minimum checked. It should be understood that healthy, check, and replace are only a few of the various types of statuses that may be used. Other embodiments may utilize addition and/or different statuses (e.g., filter cleaning recommended, etc.). Further, the statuses may be in different formats as well (e.g., a numeric value corresponding to a scale of healthy to dirty filters, such as 1-10, a color coding such as red to green to indicate healthy (green) and dirty (red), etc.). Accordingly, all such variations are intended to fall within the spirit and scope of the present disclosure.

The results of the comparison may also be provided to the user. For example, if the estimated ΔP exceeds the reference value, then an indication may be provided to a user. In this regard, a user or operator may readily see and examine how their filter is determined to be operating.

Figure 12:
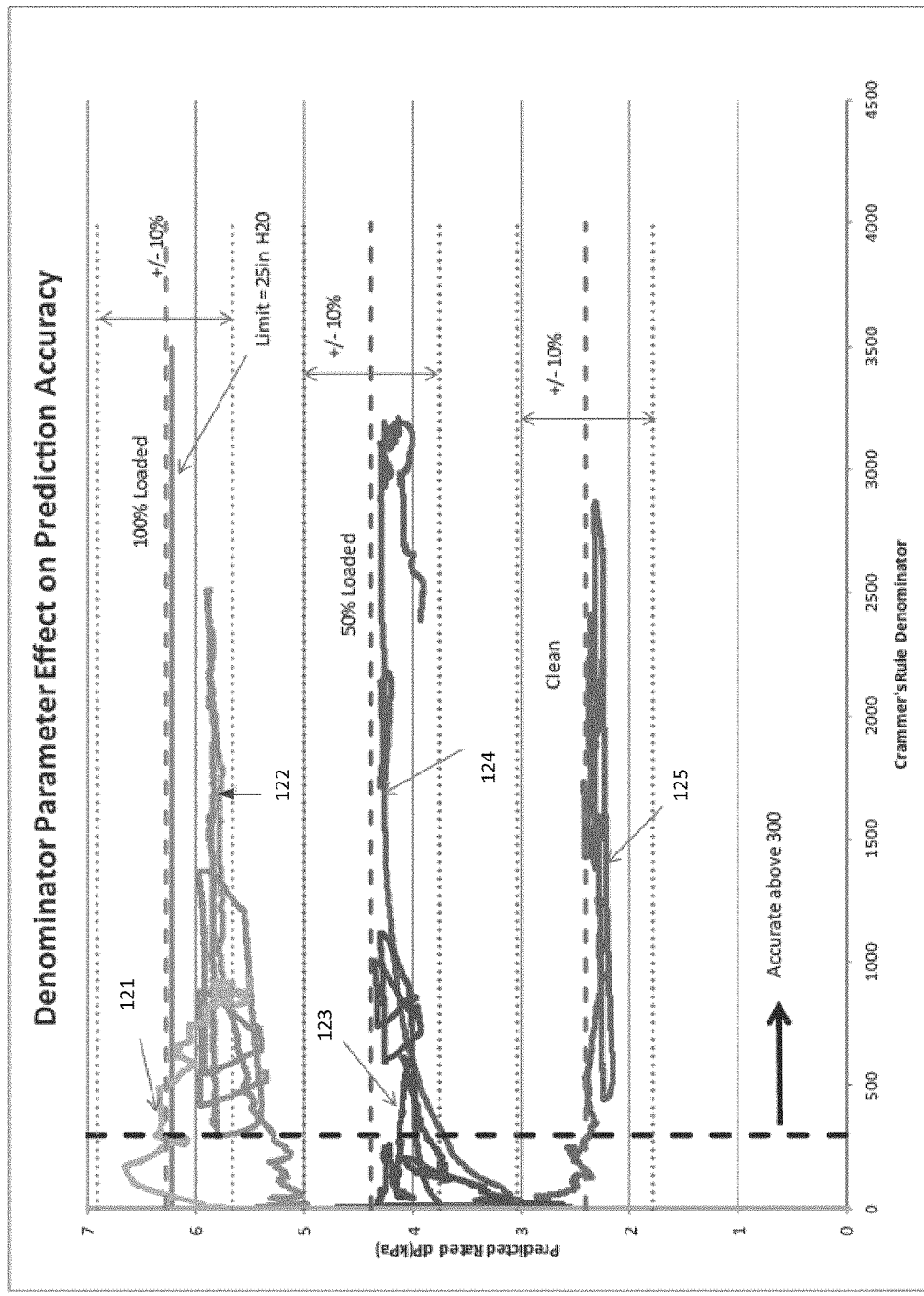
FIG. 12 is a graph illustrating the effect of manipulation of the denominator from Cramer's Rule on the accuracy of the method of FIG. 3 for estimating $\Delta P$ according to an exemplary embodiment.

In order to ensure accurate estimations for ΔP, the algorithm may be calibrated in some embodiments. For example, the algorithm may be calibrated based on the filter constants $C_1$ and $C_2$. The algorithm also may be calibrated by using a threshold value for the denominator term (Den). FIG. 12 illustrates the effect of manipulation of the denominator from Cramer's Rule on the accuracy of the method of FIG. 3. Curve 121 represents the situation of a 100% loaded filter on a dynamic cycle. Curve 122 represents the situation of a 100% loaded filter on a static cycle. Curve 123 represents the situation of a 50% loaded filter on a static cycle. Curve 124 represents the situation of a 50% loaded filter on a dynamic cycle. Curve 125 represents the situation of a clean filter on a static cycle.

Figure 13:
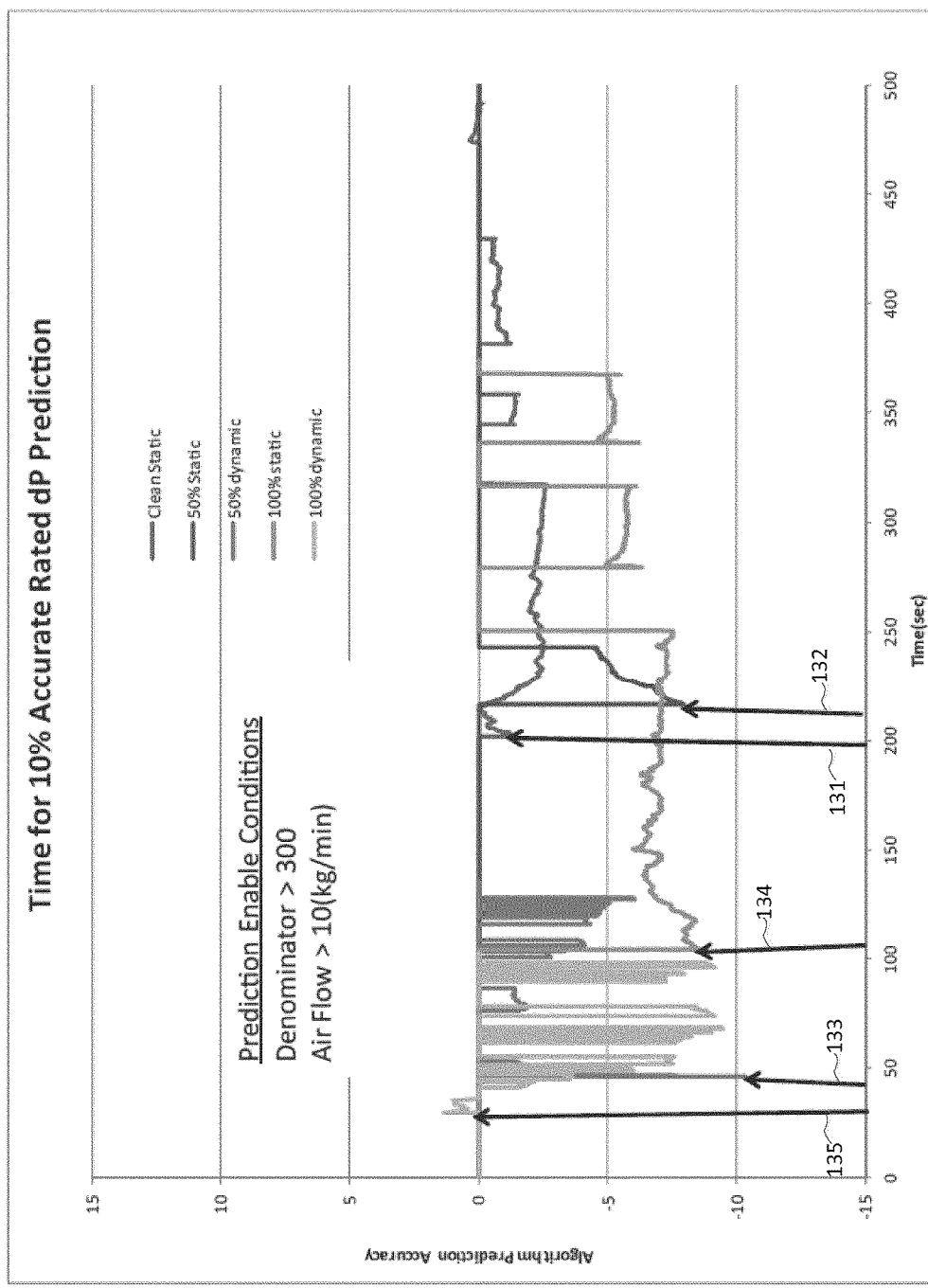
FIG. 13 is a graph illustrating the time required for the method of FIG. 3 to estimate $\Delta P$ that is accurate within ±10% error for a given Cramer's Rule denominator greater than 300 and a mass air flow greater than 10 kg/min.

FIG. 13 illustrated the time required for the method of FIG. 3 to estimate ΔP that is accurate within ±10% error for a given Cramer's Rule denominator greater than 300 and a mass air flow greater than 10 kg/min. Curve 131 represents the situation of a clean filter on a static cycle. Curve 132 represents the situation of a 50% loaded filter on a static cycle. Curve 133 represents the situation of a 50% loaded filter on a dynamic cycle. Curve 134 represents the situation of a 100% loaded filter on a static cycle. Curve 135 represents the situation of a 100% loaded filter on a dynamic cycle.

It should be noted that the processes of the methods described herein may be utilized with the other methods, although described in regard to a particular method. It should further be noted that the term "example" as used herein to describe various embodiments is intended to indicate that such embodiments are possible examples, representations, and/or illustrations of possible embodiments (and such term is not intended to connote that such embodiments are necessarily extraordinary or superlative examples).

Example and non-limiting module implementation elements include sensors (e.g., coupled to the components and/or systems in FIG. 2) providing any value determined herein, sensors providing any value that is a precursor to a value determined herein, datalink and/or network hardware including communication chips, oscillating crystals, communication links, cables, twisted pair wiring, coaxial wiring, shielded wiring, transmitters, receivers, and/or transceivers, logic circuits, hard-wired logic circuits, reconfigurable logic circuits in a particular non-transient state configured according to the module specification, any actuator including at least an electrical, hydraulic, or pneumatic actuator, a solenoid, an op-amp, analog control elements (springs, filters, integrators, adders, dividers, gain elements), and/or digital control elements.

The schematic flow chart diagrams and method schematic diagrams described above are generally set forth as logical flow chart diagrams. As such, the depicted order and labeled steps are indicative of representative embodiments. Other steps, orderings and methods may be conceived that are equivalent in function, logic, or effect to one or more steps, or portions thereof, of the methods illustrated in the schematic diagrams.

Additionally, the format and symbols employed are provided to explain the logical steps of the schematic diagrams and are understood not to limit the scope of the methods illustrated by the diagrams. Although various arrow types and line types may be employed in the schematic diagrams, they are understood not to limit the scope of the corresponding methods. Indeed, some arrows or other connectors may be used to indicate only the logical flow of a method. For instance, an arrow may indicate a waiting or monitoring period of unspecified duration between enumerated steps of a depicted method. Additionally, the order in which a particular method occurs may or may not strictly adhere to the order of the corresponding steps shown. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like Modules may also be implemented in machine-readable medium for execution by various types of processors. An identified module of executable code may, for instance, comprise one or more physical or logical blocks of computer instructions, which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of computer readable program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in machine-readable medium (or computer-readable medium), the computer readable program code may be stored and/or propagated on in one or more computer readable medium(s).

The computer readable medium may be a tangible computer readable storage medium storing the computer readable program code. The computer readable storage medium may be, for example, but not limited to, an electronic, magnetic, optical, electromagnetic, infrared, holographic, micromechanical, or semiconductor system, apparatus, or device, or any suitable combination of the foregoing.

More specific examples of the computer readable medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store computer readable program code for use by and/or in connection with an instruction execution system, apparatus, or device.

The computer readable medium may also be a computer readable signal medium. A computer readable signal medium may include a propagated data signal with computer readable program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport computer readable program code for use by or in connection with an instruction execution system, apparatus, or device. Computer readable program code embodied on a computer readable signal medium may be transmitted using any appropriate medium, including but not limited to wireless, wireline, optical fiber cable, Radio Frequency (RF), or the like, or any suitable combination of the foregoing.

In one embodiment, the computer readable medium may comprise a combination of one or more computer readable storage mediums and one or more computer readable signal mediums. For example, computer readable program code may be both propagated as an electro-magnetic signal through a fiber optic cable for execution by a processor and stored on RAM storage device for execution by the processor.

Computer readable program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The computer readable program code may execute entirely on the user's computer, partly on the user's computer, as a stand-alone computer-readable package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The program code may also be stored in a computer readable medium that can direct a computer, other programmable data processing apparatus, or other devices to function in a particular manner, such that the instructions stored in the computer readable medium produce an article of manufacture including instructions which implement the function/act specified in the schematic flowchart diagrams and/or schematic block diagrams block or blocks.

Accordingly, the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A method, comprising:
receiving upstream mass air flow data indicative of a mass air flow on an upstream side of an air filter;
receiving downstream air pressure data indicative of an air pressure on a downstream side of the air filter;
receiving downstream temperature data indicative of a temperature on the downstream side of the air filter;
determining a differential pressure ($\Delta P$) across the air filter indicative of a loading of the air filter based on the upstream mass air flow data, the downstream air pressure data, and the downstream temperature data;
comparing the determined differential pressure with a reference value; and
determining a status of the air filter based on the comparison, and providing an output indicating the status of the air filter.

2. The method of claim 1, wherein the status is healthy responsive to the differential pressure being less than the reference value.

3. The method of claim 1, wherein the status is at least one of replace and check responsive to the differential pressure greater than or equal to the reference value.

4. The method of claim 3, wherein the status is replace if the differential pressure is greater than the reference value by a first amount, wherein the status is check if the differential pressure is greater than the reference value by a second amount, wherein the first amount is greater than the second amount.

5. The method of claim 1, wherein differential pressure includes at least one of a laminar pressure loss and a turbulent pressure loss.

6. The method of claim 1, wherein differential pressure is a rated flow differential pressure, and wherein said determining differential pressure follows a formula:

$$\Delta P = P_{amb} - P_{sensor} = \frac{1}{\rho}(C_1 M + C_2 M^2),$$

wherein $P_{amb}$ is an air pressure on the upstream side of the air filter;
wherein $P_{sensor}$ is the air pressure on the downstream side of the air filter;
wherein $C_1$ is a coefficient representing a laminar pressure loss across the air filter;
wherein $C_2$ is a coefficient representing a turbulent pressure loss across the air filter;
wherein M is a rated flow representing a designed operating flow; and
wherein $\rho$ is an air density of the downstream side of the air filter determined by:

$$\rho = \frac{P_{sensor}}{RT},$$

wherein T is the temperature on the downstream side of the air filter; and
wherein R is a gas constant.

7. The method of claim 6, wherein the air pressure on the upstream side ($P_{amb}$) and the coefficients ($C_1$ and $C_2$) are determined by applying a least squares method to a plurality of upstream mass air flows, a plurality of downstream air pressures, and a plurality of downstream temperatures.

8. A system, comprising:
an air filter; and
a processing system communicably coupled to the air filter, the processing system structured to:
receive upstream mass air flow data indicative of a mass air flow on an upstream side of an air filter;
receive downstream air pressure data indicative of an air pressure on a downstream side of the air filter;
receive downstream temperature data indicative of a temperature on the downstream side of the air filter;
determine a differential pressure ($\Delta P$) across the air filter indicative of a loading of the air filter based on the upstream mass air flow data, the downstream air pressure data, and the downstream temperature data;
compare the determined differential pressure with a reference value;
determine a status of the air filter based on the comparison, the status providing an indication of how the air filter is operating; and
provide an output indicating the status of the air filter.

9. The system of claim 8, wherein the status is healthy responsive to the differential pressure being less than the reference value.

10. The method of claim 8, wherein the status is at least one of replace and check responsive to the differential pressure greater than or equal to the reference value.

11. The method of claim 8, wherein the status is replace if the differential pressure is greater than the reference value by a first amount, wherein the status is check if the differential pressure is greater than the reference value by a second amount, wherein the first amount is greater than the second amount.

12. An apparatus, comprising:
an upstream mass air flow module structured to receive upstream mass air flow data indicative of a mass air flow on an upstream side of an air filter;

a downstream air pressure module structured to receive downstream air pressure data indicative of an air pressure on a downstream side of the air filter;

a downstream temperature module structured to receive downstream temperature data indicative of a temperature on the downstream side of the air filter;

a differential pressure module structured to determine a differential pressure (ΔP) across the air filter indicative of a loading of the air filter based on the upstream mass air flow data, the downstream air pressure data, and the downstream temperature data; and an indication module structured to compare the determined differential pressure with a reference value to determine a status of the air filter based on the comparison, the status providing an indication of how the air filter is operating, and providing an output indicating the status of the air filter.

13. The apparatus of claim 12, wherein the status includes one of healthy, replace, and check based on the comparison between the determined differential pressure and the reference value, wherein the status is healthy responsive to the differential pressure being less than the reference value, and wherein the status is at least one of replace and check responsive to the differential pressure greater than or equal to the reference value.

14. The apparatus of claim 12, wherein differential pressure is a rated flow differential pressure, and wherein the differential pressure module is further structured to determine differential pressure as follows:

$$\Delta P = P_{amb} - P_{sensor} = \frac{1}{\rho}(C_1 M + C_2 M^2),$$

wherein $P_{amb}$ is an air pressure of the upstream side of the air filter;

wherein $P_{sensor}$ is the air pressure of the downstream side of the air filter obtained from the air pressure sensor;

wherein $C_1$ is a coefficient representing a laminar pressure loss;

wherein $C_2$ is a coefficient representing a turbulent pressure loss;

wherein M is a rated flow representing a designed operating flow; and wherein $\rho$ is an air density of the downstream side of the air filter determined as:

$$\rho = \frac{P_{sensor}}{RT},$$

wherein T is the temperature of the downstream side of the air filter; and wherein R is a gas constant.

15. The apparatus of claim 14, wherein the air pressure on the upstream side ($P_{amp}$) and the coefficients ($C_1$ and $C_2$) are determined by applying a least squares method to a plurality of upstream mass air flows, a plurality of downstream air pressures, and a plurality of downstream.

16. The apparatus of claim 15, wherein the upstream side ($P_{amp}$) and the coefficients ($C_1$ and $C_2$) are determined as follows:

$$P_{amb} = \frac{\text{Det}\begin{bmatrix} [k_i^2 P_{sensor,i}^3] & [-k_i P_{sensor,i} M_i] & [-k_i P_{sensor,i} M_i^2] \\ [-k_i P_{sensor,i}^2 M_i] & [M_i^2] & [M_i^3] \\ [-k_i P_{sensor,i}^2 M_i^2] & [M_i^3] & [M_i^4] \end{bmatrix}}{Den},$$

$$C_1 = \frac{\text{Det}\begin{bmatrix} [k_i^2 P_{sensor,i}^2] & [k_i^2 P_{sensor,i}^3] & [-k_i P_{sensor,i} M_i^2] \\ [-k_i P_{sensor,i} M_i] & [-k_i P_{sensor,i}^2 M_i] & [M_i^3] \\ [-k_i P_{sensor,i} M_i^2] & [-k_i P_{sensor,i}^2 M_i^2] & [M_i^4] \end{bmatrix}}{Den},$$

$$C_2 = \frac{\text{Det}\begin{bmatrix} [k_i^2 P_{sensor,i}^2] & [-k_i P_{sensor,i} M_i] & [k_i^2 P_{sensor,i}^3] \\ [-k_i P_{sensor,i} M_i] & [M_i^2] & [-k_i P_{sensor,i}^2 M_i] \\ [-k_i P_{sensor,i} M_i^2] & [M_i^3] & [-k_i P_{sensor,i}^2 M_i^2] \end{bmatrix}}{Den},$$

$$Den = \text{Det}\begin{bmatrix} [k_i^2 P_{sensor,i}^2] & [-k_i P_{sensor,i} M_i] & [-k_i P_{sensor,i} M_i^2] \\ [-k_i P_{sensor,i} M_i] & [M_i^2] & [M_i^3] \\ [-k_i P_{sensor,i} M_i^2] & [M_i^3] & [M_i^4] \end{bmatrix},$$

wherein Det[matrix] is a determinant of the matrix;

wherein $M_i$ is an i-th mass air flow of the plurality of mass air flows obtained from the mass air flow sensor;

wherein $P_{sensor,i}$, is an i-th air pressure of the plurality of air pressures obtained from the air pressure sensor;

wherein $k_i$ is calculated as $k_i = 1000/(RT_i)$, $T_i$ being an i-th temperature of the plurality of temperatures obtained from the temperature sensor; and wherein $[X_i]$ is an average of the plurality of X.

17. The apparatus of claim 12, further comprising a calibration module structured to calibrate at least one of the coefficients ($C_1$ and $C_2$) and the denominator (Den) empirically.

* * * * *